(12) United States Patent
Feng et al.

(10) Patent No.: US 10,089,451 B2
(45) Date of Patent: Oct. 2, 2018

(54) ELECTROCARDIOGRAM (ECG)-BASED AUTHENTICATION APPARATUS AND METHOD THEREOF, AND TRAINING APPARATUS AND METHOD THEREOF FOR ECG-BASED AUTHENTICATION

(71) Applicant: Samsung Electronics Co., Ltd., Suwon-si (KR)

(72) Inventors: Xuetao Feng, Beijing (CN); Chao Zhang, Beijing (CN); Chisung Bae, Yongin-si (KR); Jongae Park, Yongin-si (KR); Sang-joon Kim, Hwaseong-si (KR); Yang Liu, Beijing (CN)

(73) Assignee: Samsung Electronics Co., Ltd., Suwon-si (KR)

( * ) Notice: Subject to any disclaimer, the term of this patent is extended or adjusted under 35 U.S.C. 154(b) by 303 days.

(21) Appl. No.: 15/041,477

(22) Filed: Feb. 11, 2016

(65) Prior Publication Data

US 2016/0232340 A1    Aug. 11, 2016

(30) Foreign Application Priority Data

Feb. 11, 2015  (CN) .......................... 2015 1 0071283
Dec. 16, 2015  (KR) ....................... 10-2015-0180291

(51) Int. Cl.
*G06F 21/00* (2013.01)
*G06F 21/32* (2013.01)
(Continued)

(52) U.S. Cl.
CPC .......... *G06F 21/32* (2013.01); *A61B 5/04525* (2013.01); *A61B 5/117* (2013.01);
(Continued)

(58) Field of Classification Search
CPC .......... G06F 21/30; G06F 21/31; G06F 21/32; H04L 9/3231; H04L 63/0861;
(Continued)

(56) References Cited

U.S. PATENT DOCUMENTS

2006/0136744 A1  6/2006  Lange
2013/0190635 A1  7/2013  Shen et al.
(Continued)

FOREIGN PATENT DOCUMENTS

CN    102323977 A    1/2012
CN    102688032 A    9/2012
(Continued)

OTHER PUBLICATIONS

"Label Consistent K-SVD: Learning a Discriminative Dictionary for Recognition", Zhoulin Jiang, Zhe Lin, and Larry S. Davis, IEEE, Transactions on Pattern Analysis and Machine Intelligence, vol. 35, No. 11, Nov. 2013, pp. 2651-2664.*
(Continued)

*Primary Examiner* — Joseph P Hirl
*Assistant Examiner* — Chi Nguy
(74) *Attorney, Agent, or Firm* — NSIP Law

(57) ABSTRACT

Provided are electrocardiogram (ECG)-based authentication and training. An authentication method includes generating a feature vector of an ECG obtained from an entity or a person based on a dictionary, classifying the ECG through a classifier based on the feature vector, and performing authentication based on a classification result.

27 Claims, 8 Drawing Sheets

(51) Int. Cl.

| | | |
|---|---|---|
| *A61B 5/0452* | (2006.01) | |
| *H04L 9/32* | (2006.01) | |
| *A61B 5/00* | (2006.01) | |
| *A61B 5/117* | (2016.01) | |
| *H04L 29/06* | (2006.01) | |
| *G06K 9/00* | (2006.01) | |
| *G06K 9/62* | (2006.01) | |
| *G16H 50/20* | (2018.01) | |

(52) U.S. Cl.
CPC .......... *A61B 5/7267* (2013.01); *G06K 9/0055* (2013.01); *G06K 9/6249* (2013.01); *G06K 9/6255* (2013.01); *H04L 9/3231* (2013.01); *H04L 63/0861* (2013.01); *G06K 2009/00939* (2013.01); *G16H 50/20* (2018.01); *H04L 2209/88* (2013.01)

(58) Field of Classification Search
CPC .................. H04L 2209/88; G06K 9/6255; G06K 9/6249; G06K 9/0055; G06K 2009/00939; G16H 50/20; A61B 5/7267; A61B 5/117; A61B 5/04525
See application file for complete search history.

(56) References Cited

U.S. PATENT DOCUMENTS

| | | | |
|---|---|---|---|
| 2013/0254861 A1 | 9/2013 | Konetski et al. | |
| 2014/0045459 A1* | 2/2014 | Hjelm ................ | H04L 63/0861 455/411 |
| 2014/0301634 A1 | 10/2014 | Ishii | |
| 2015/0028996 A1* | 1/2015 | Agrafioti ................ | G06F 21/40 340/5.82 |

FOREIGN PATENT DOCUMENTS

| | | |
|---|---|---|
| CN | 102968618 A | 3/2013 |
| CN | 103892821 A | 7/2014 |
| CN | 103971123 A | 8/2014 |
| CN | 104200203 A | 12/2014 |
| CN | 104224205 A | 12/2014 |
| CN | 104281845 A | 1/2015 |
| KR | 10-2006-0082677 A | 7/2006 |
| KR | 10-2013-00050817 A | 5/2013 |

OTHER PUBLICATIONS

"Ambiguously Labeled Learning Using Dictionaries", Yi-Chen Chen, Vishal M. Patel, Rama Chellappa and P. Jonathon Phillips, IEEE, Transactions on Information Forensics and Security, vol. 9, No. 12, Dec. 2014, pp. 2076-2088.*
Yoon, T., Assessmemt of Biometric Features for Human Identification from ECG by Modified Autoassociative Neural Network (MANN), Konkuk University Department of Biomedical Engineering, Creative Commons, 2011 (122 pages).
F. Sufi, et al., "Polynomial distance measurement for ECG based biometric authentication," *Security and Communication Networks*, Vo. 3, Issue 4, Jul. 2010, pp. 303-319.
M. M. Tantawi, et al., "Fiducial feature reduction analysis for electrocardiogram (ECG) based biometric recognition," *Journal of Intelligent Information Systems*, vol. 40, No. 1, Jul. 2012, pp. 17-39.
M. E. Naraghi, et al., "Human Identification Using ECG Feature Extracted from Innovation Signal of Extended Kalman Filter," *Proceedings of the 5$^{th}$ International Conference on BioMedical Engineering and Informaties*, (BMEI 2012), Oct. 2012, pp. 545-549.
D. P. Coutinho, et al., "Novel fiducial and non-fiducial approaches to electrocardiogram-based biometric systems," IEEE IET Biometrics, vol. 2, Issue 2, Jun. 2013, pp. 64-75.
J. Wang, et al., "Human Identification From ECG Signals Via Sparse Representation of Local Segments," *IEEE Signal Processing Letters*, vol. 20, No. 10, Oct. 2013, pp. 937-940.
S. Venugopalan, et al., "Analysis of Low-Dimensional Radio-Frequency Impedence-Based Cardio-Synchronous Waveforms for Biometric Authentication," *IEEE Transactions Biomedical Engineering*, vol. 61, No. 8, Aug. 2014, pp. 2324-2335.
M. Balouchestani, et al., "Advanced K-means clustering algorithm for large ECG data sets based on a collaboration of compressed sensing theory and K-SVD approach," *Signal, Image and Video Processing*, vol. 10, No. 1, Nov. 2014, pp. 113-120.
Partial European Search Report dated May 4, 2016, in European Application No. 16154997.7 (11 pages, in English).
Chinese Office Action dated Jul. 4, 2018 in Chinese Patent Application No. 201510071283.3 (13 pages in Chinese).

* cited by examiner

ELECTROCARDIOGRAM (ECG)-BASED AUTHENTICATION APPARATUS AND METHOD THEREOF, AND TRAINING APPARATUS AND METHOD THEREOF FOR ECG-BASED AUTHENTICATION

CROSS-REFERENCE TO RELATED APPLICATION(S)

This application claims the benefit under 35 USC 119(a) of Chinese Patent Application No. 201510071283.3, filed on Feb. 11, 2015, in the Chinese Patent Office, and Korean Patent Application No. 10-2015-0180291, filed on Dec. 16, 2015, in the Korean Intellectual Property Office, the entire disclosures of which are incorporated herein by reference for all purposes.

BACKGROUND

1. Field

The following description relates to signal processing apparatus and method thereof, more particularly, to pattern identification, and further particularly, to electrocardiogram (ECG)-based authentication apparatus and method thereof.

2. Description of Related Art

With the development of science technology, various methods are used to verify an identity of a user or a person through biometric features. The biometric feature-based authentication identifies an entity, for example, the person, based on unique biological or behavioral features, for example, an iris, a fingerprint, a face, a voice, or a gait of the person. When compared to traditional authentication, the biometric feature-based authentication provides high-accuracy authentication. However, such biometric feature-based authentication requires some confirmation. For example, in a case of a portion of the biometric features, such as a fingerprint, a face, and a voice, security of an authentication system may be weakened by a forged or falsified fingerprint or face, or a pre-recorded voice.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an embodiment, there is provided a method, including: generating a feature vector from an electrocardiogram (ECG) based on a pre-trained dictionary; generating a classification result of the ECG based on the feature vector and a pre-trained classifier; and performing authentication of the ECG based on the classification result.

The method may further include: synchronously training the dictionary and the classifier.

The dictionary may include category dictionaries corresponding to categories, and the classifier may include category classifiers corresponding to the categories.

The dictionary and the classifier may be synchronously trained by generating feature vectors to train ECGs based on the category dictionaries, determining prediction categories for the ECGs based on the feature vectors, and alternately updating the category dictionaries and the category classifiers based on the categories and the prediction categories.

The generating of the feature vector may include: determining coefficients of category dictionaries included in the dictionary for the ECG to be a linear combination of the category dictionaries; and generating the feature vector based on the coefficients.

The generating of the feature vector may include: dividing the ECG into a signal segment; generating a feature indication corresponding to the signal segment; generating a second feature indication by performing group sparse coding, based on the dictionary, of the feature indication; and generating the feature vector based on the second feature indication.

The feature indication may be a linear combination of a portion of category dictionaries included in the dictionary, and the second feature indication may include coefficients of the portion of the category dictionaries.

The generating of the classification result may include: generating a label corresponding to a classification result of a signal segment of the ECG based on the feature vector and the classifier; and generating the classification result of the ECG based on the label.

The performing may include: obtaining a classification result of a reference ECG; and performing the authentication based on a voting mechanism for the classification result of the ECG and the classification result of the reference ECG.

The reference ECG may include a reference signal segment, wherein the performing of the authentication based on the voting mechanism may include: generating a first distribution including a number of signal segments belonging to each of a plurality of categories based on a label of the ECG; obtaining a second distribution including a number of reference signal segments belonging to each of the categories; calculating a similarity between the first distribution and the second distribution; and performing the authentication by comparing the similarity to a threshold.

The classification result of the reference ECG may be obtained by applying the dictionary and the classifier to the reference ECG.

In accordance with an embodiment, there is provided a training method, including: generating feature vectors of training electrocardiograms (ECGs) based on category dictionaries corresponding to categories; determining prediction categories for the training ECGs based on the feature vectors; and alternately updating the category dictionaries and category classifiers based on the categories and the prediction categories.

The generating may include: dividing each of the training ECGs into a signal segment; generating a feature indication corresponding to the signal segment; generating a second feature indication by performing group sparse coding, based on the category dictionaries, of the feature indication; and generating the feature vectors based on the second feature indication corresponding to the signal segment.

The updating may include: fixing the category classifiers, and optimizing the category dictionaries to minimize an error between the prediction categories and the categories; and fixing the optimized category dictionaries, and optimizing the category classifiers to minimize the error between the prediction categories and the categories, wherein the optimizing of the category dictionaries and the optimizing of the category classifiers are synchronously iterated.

The optimizing of the category dictionaries may include optimizing the category dictionaries to minimize the error using a gradient descent algorithm, and the optimizing of the category classifiers may include optimizing the category classifiers to minimize the error using the gradient descent algorithm.

The method may further include: terminating the updating in response to the optimizing of the category dictionaries and the optimizing of the category classifiers satisfying a condition; and outputting the updated category dictionaries and the updated category classifiers, wherein the condition may include at least one of a condition in which an iteration count reaches a value, a condition in which the error is less than a first value, and a condition in which a variation in the error is less than a second value.

The method may further include: initializing the category dictionaries based on the training ECGs corresponding to the categories.

The initializing may include: preprocessing the training ECGs; generating clusters by clustering the preprocessed training ECGs based on the categories; and generating the initialized category dictionaries by normalizing centers of the clusters.

The preprocessing may include: dividing the training ECGs into a signal segment; extracting a feature of the signal segment; and generating a feature indication of the signal segment by performing dimension reduction processing of the feature.

The dividing may include: filtering each of the training ECGs; detecting a QRS wave of each of the filtered training ECGs; and generating the at least one signal segment based on a result of the detecting.

The method may further include: initializing the category classifiers based on the feature vectors and the category dictionaries.

The initializing may include: generating a probability distribution of the categories of the signal segment based on the feature vectors and the category dictionaries; calculating a prediction error for the signal segment based on the probability distribution and an actual category of the signal segment; obtaining category classifiers minimizing an error between the prediction categories and the categories based on the prediction error; and generating the initialized category classifiers as the obtained category classifiers.

The method may further include: generating a dictionary by merging the updated category dictionaries; and generating a classifier by merging the updated category classifiers.

In accordance with an embodiment, there is provided a non-transitory computer-readable storage medium including a program including instructions to cause a computer to perform the method described above.

In accordance with an embodiment, there is provided an apparatus, including: a sensor configured to receive an electrocardiogram (ECG); and a processor configured to generate a feature vector of the ECG based on a pre-trained dictionary, generate a classification result of the ECG based on the feature vector and a pre-trained classifier, and perform authentication of the ECG based on the classification result.

In accordance with an embodiment, there is provided a training apparatus, including: a sensor configured to receive training electrocardiograms (ECGs); and a processor configured to generate feature vectors of training ECGs based on category dictionaries corresponding to categories, determine prediction categories for the training ECGs based on the feature vectors, and alternately update the category dictionaries and category classifiers based on the categories and the prediction categories.

In accordance with an embodiment, there is provided a method, including: dividing an electrocardiogram (ECG) for user authentication into a signal segment; generating a first feature indication corresponding to the signal segment; generating a second feature indication by performing group sparse coding, based on a dictionary and the first feature indication; generating a feature vector of the ECG based on the second feature indication corresponding to the signal segment; generating a classification result indicative of the ECG based on the feature vector and a classifier; and performing authentication of the ECG based on the generated classification result.

The method may further include: extracting a feature from the divided signal segment; and performing dimension reduction processing of the extracted feature.

The generating of the classification result may be based on a label corresponding to a classification result of the signal segment of the ECG based on the feature vector and the pre-trained classifier.

The method may further include: synchronously training the dictionary and the pre-trained classifier.

Other features and aspects will be apparent from the following detailed description, the drawings, and the claims.

Figure 1:
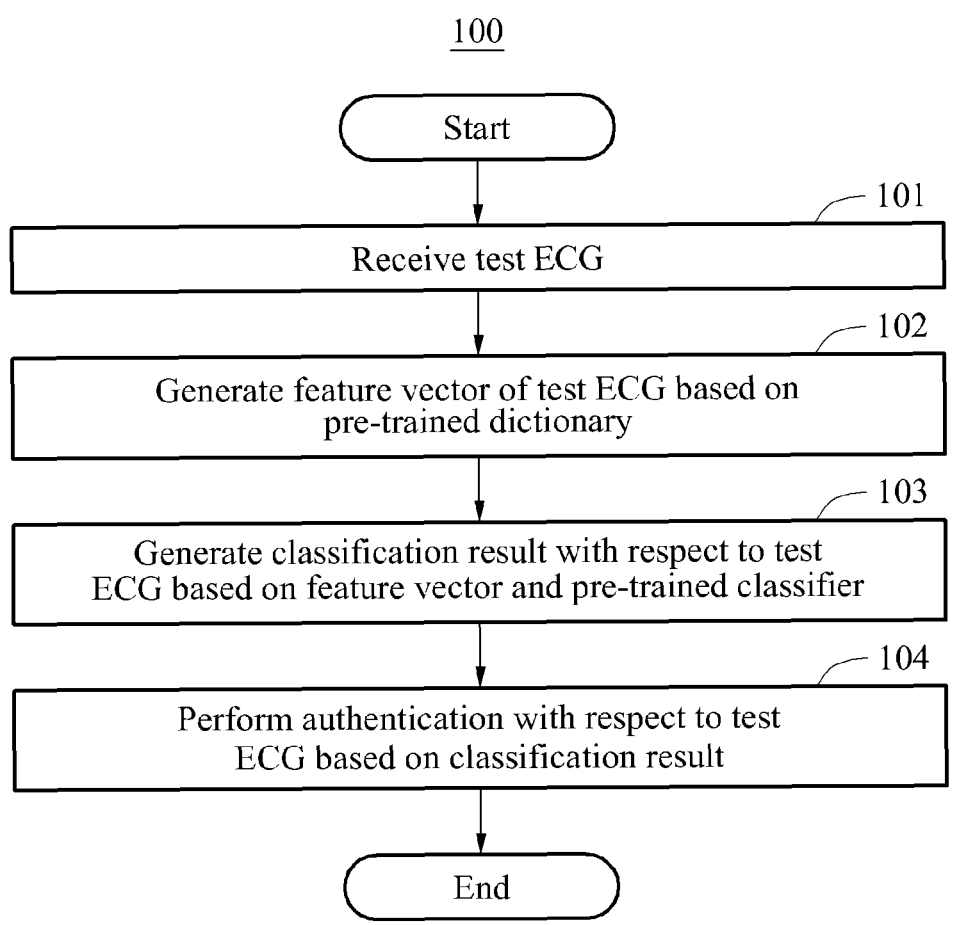
FIG. 1 is a flowchart illustrating an electrocardiogram (ECG)-based authentication method, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Specific structural or functional descriptions of examples provided in the present disclosure are exemplary to merely describe the examples. The examples may be modified and implemented in various forms, and the scope of the examples is not limited to the descriptions provided in the present specification.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Examples may be implemented as various types of products, for example, personal computers, laptop computers, tablet computers, smart phones, televisions, smart home appliances, intelligent vehicles, kiosks, and wearable devices. For example, the examples are applicable to user recognition using a smart phone, a mobile device, and a smart home system. The examples are applicable to a payment service through user recognition. Further, the examples are also applicable to an intelligent automobile system which automatically starts up an engine by recognizing a user. Hereinafter, reference will now be made in detail to the examples or embodiments with reference to the accompanying drawings, wherein like reference numerals refer to like elements throughout.

Electrocardiogram (ECG)-based authentication performs verification and authentication of an identity of an entity, such as a person, using an ECG. Among biometric feature-based authentications, ECG-based authentication provides a relatively high stability. An ECG is difficult to forge or falsify, is obtained at low cost, and provides high-level discrimination. Thus, the ECG is an emerging issue in a field of security technology.

In many cases, ECG-based authentication is used in a security area in which stability is significant and; thus, a high-level accuracy is needed. To achieve the high-level accuracy, a feature with high-level discrimination needs to be extracted. An ECG of the same person provides different readings when the person is in different physiological states, for example, a stationary state and a state after exercising. Further, the ECG of the same person may vary due to age, health, or activities endured during a day at different time periods. Because the ECG of the same person shows different readings, different categories are used to classify the ECG. Accordingly, in ECG-based authentication, learning a satisfactory feature, with discrimination, with respect to signals collected in different physiological states of the same person and at different time periods is needed for accurate authentication.

ECG-based authentication is applicable to various types of electronic devices. The electronic devices include electrocardiographs, and are used to collect ECGs of living bodies, including persons or animals. The electronic devices include desktop computers, laptop computers, smart phones, tablet PCs, personal digital assistants (PDAs), smart security devices, gate security devices, smart architecture devices, and automobile electronic devices. However, the examples are not limited thereto.

An ECG-based authentication method is applied to an electronic device to verify an identity of a person and determine whether the person has an authority for use or whether the user obtains access through a proper route based on an ECG of the person. An identity of a user is verified based on an ECG of the user, and information related to the user is additionally retrieved or recorded based on the identity of the user. The ECG-based authentication method is applicable to identify verification in various ways. For example, the ECG-based authentication method is utilized for user access control, financial transactions, airport check-in and boarding, patient privacy protection, and border security. However, the examples of various utilizations or applications are not limited thereto.

In accordance with an example, a reference ECG is a pre-stored ECG. The reference ECG is obtained from each user, pre-stored, and compared with a test ECG to perform user authentication. The test ECG is an ECG to be tested for user authentication. The test ECG is input from a user.

A reference ECG of each user is obtained by collecting a single ECG of the user and matching the ECG to the user. In another example, a reference ECG of each user is obtained by collecting a plurality of ECGs of the user and matching a single representative ECG to the user. The single representative ECG is obtained through selection/synthesis with respect to the plurality of ECGs.

The test ECG is a signal to be used for authentication. The test ECG is obtained from the user to be authenticated. In a case in which authentication with respect to an identity of a new user is required, a test ECG needs to be conducted and obtained from the user to be authenticated. The test ECG of the user is obtained by obtaining a single ECG of the user. In another example, the test ECG of the user is a single representative ECG obtained through selection/synthesis with respect to a plurality of ECGs of the user. A method to conduct and obtain a test ECG of the user to be authenticated is not limited to the examples described above. Various types of ECG testing may be adopted.

An ECG-based authentication method includes four operations, including data preprocessing, valid feature indication or feature extraction, robust authentication mechanism, and reasonable decision mechanism. A feature used in the authentication method is extracted from a primitive ECG signal segment, and indicates information related to a time domain or a frequency domain. The feature is a low-level non-discriminative feature and; thus, information to be used to identify the user may be omitted. Further, in the ECG-based authentication method, the feature extraction and the authentication mechanism are separately performed or executed. Thus, label information of a signal is not consecutively used, and mutual compensation between the feature extraction and the authentication mechanism is not possible. Accordingly, the accuracy of the ECG-based authentication method is low.

In accordance with an embodiment, an ECG-based authentication method is described that synchronously trains a dictionary and a classifier to mutually promote acquisition of a feature with high-level discrimination, thereby obtaining a classifier with high accuracy.

Hereinafter, examples will be described with reference to FIGS. 1 through 8. In detail, the ECG-based authentication will be described with reference to FIGS. 1, 6, and 7, and a training for the ECG-based authentication will be described with reference to FIGS. 4 through 6.

FIG. 1 is a flowchart 100 illustrating an ECG-based authentication method, in accordance with an embodiment.

An ECG-based authentication apparatus (to be described with reference to FIG. 8) operates using the ECG-based authentication method, and performs authentication based on pre-trained dictionary and a pre-trained classifier. The pre-trained dictionary and the pre-trained classifier used by the authentication apparatus are synchronously pre-trained using a training method for ECG-based authentication. The pre-trained dictionary includes category dictionaries of a plurality of categories, and the pre-trained classifier includes category classifiers of the plurality of categories.

The pre-trained dictionary and the pre-trained classifier are synchronously trained by generating a plurality of feature vectors to train ECGs based on the category dictionaries, determining prediction categories to train the ECGs based on the plurality of feature vectors, and, alternately, updating the category dictionaries and the category classifiers based on the categories and the determined prediction categories.

To express an ECG as a linear combination of the category dictionaries included in the dictionary, coefficients of the category dictionaries are determined, and a feature vector is generated based on the determined coefficients. The ECG is divided into at least one signal segment, at least one first feature indication is generated that corresponds to the at least one signal segment, and at least one second feature indication is generated by performing group sparse coding, based on the dictionary, with respect to the at least first feature indication. The feature vector is generated based on the at least one second feature indication. The first feature indication is expressed as a linear combination of a portion of the plurality of category dictionaries included in the dictionary. The second feature indication includes coefficients of the portion of the category dictionaries.

Referring to FIG. 1, in operation 101, the authentication apparatus receives a test ECG. The test ECG is an ECG to be used for authentication. The test ECG is obtained from an entity, such as a person, through a sensor to authenticate the entity.

The authentication apparatus extracts a feature with discrimination from the test ECG by preprocessing the received test ECG. In detail, the preprocessing performed on the test ECG by the authentication apparatus includes dividing the test ECG into at least one signal segment, extracting a feature from the at least one divided signal segment, performing dimension reduction processing with respect to the extracted feature, and generating a first feature indication corresponding to the at least one signal segment.

The preprocessing performed by the authentication apparatus also includes removing an occurring noise signal by performing data filtering on the collected test ECG, and detecting a QRS wave from the filtered test ECG. The "ORS complex" is a combination of the Q wave, R wave and S wave and represents ventricular depolarization. A normal duration (interval) of the QRS complex is 0.08 and 0.10 seconds (80 and 100 ms). When the duration is between 0.10 and 0.12 seconds it is intermediate or slightly prolonged. A QRS duration of greater than 0.12 seconds is considered abnormal.

The preprocessing performed by the authentication apparatus includes dividing the test ECG into the signal segment based on a result of detecting a QRS wave from the test ECG, and generating the first feature indication corresponding to the at least one divided signal segment.

Figure 2:
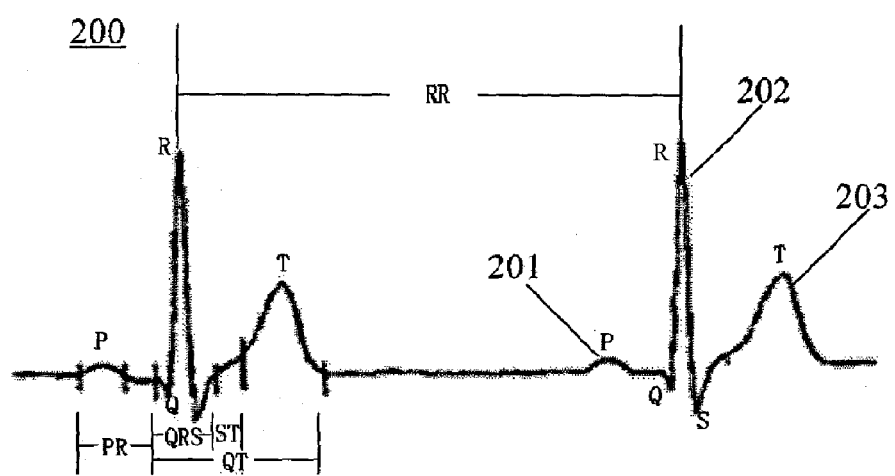
FIG. 2 illustrates a waveform of an ECG, in accordance with an embodiment.

FIG. 2 illustrates a waveform of an ECG, in accordance with an embodiment.

An ECG is a signal showing a periodic electrical activity of a heart. FIG. 2 is an example of a waveform of a typical ECG. Referring to FIG. 2, the typical ECG includes a P wave 201, a QRS wave 202, and a T wave 203. A wave first shown in the ECG is the P wave 201. The P wave 201 indicates atrial depolarization. The QRS wave 202 indicates a potential variation in ventricular depolarization. The QRS wave 202 includes three successive waves. In general, a first downward wave is referred to as a Q wave, a first upward wave following the Q wave is referred to as an R wave, and a single downward wave connecting to a descent of the R wave is referred to as an S wave. The three Q, R, and S waves are connected to each other. In general, a total width or time of the three waves does not exceed 0.12 seconds (s). The three waves are collectively referred to as a QRS wave group. The T wave 203 is a single wave with a relatively low amplitude shown after an ST segment and a relatively long occupation and use time, and indicates a potential variation in ventricular repolarization.

Energy of the QRS wave occupies a relatively large portion of the ECG, and includes a significant feature parameter of the ECG. Detection of the QRS wave is useful to divide the ECG. Valid information related to the QRS wave group is obtained through the detection of the QRS wave. An operation of filtering the ECG and detecting waves from the ECG, the operation performed in the preprocessing, is not limited to a specific technical field, and may be implemented other similar processes.

The authentication apparatus divides the ECG into one or more signal segments based on a result of detecting the QRS wave. In an example, the divided signal segment corresponds to a single heart beat or a plurality of heart beats.

The authentication apparatus extracts a feature of each of the divided signal segments. For example, the features includes at least one of a time domain feature, a frequency domain feature, and a statistical feature of the signal segment, or a combination thereof. The time domain feature includes a waveform of the ECG, an occurrence moment of a predetermined waveform, for example, a crest moment of a T wave, a change moment, and a continuous time. However, examples of the time domain feature are not limited thereto. The frequency domain feature includes a frequency of an ECG, and a spectral distribution. However, examples of the frequency domain feature are not limited thereto.

The authentication apparatus obtains the first feature indication of each of the at least one signal segment by performing dimension reduction processing using a principal component analysis (PCA) or a linear discriminant analysis (LDA) with respect to the extracted feature as the preprocessing. Both linear discriminant analysis (LDA) and principal component analysis (PCA) are linear transformation techniques that are commonly used for dimensionality reduction. PCA can be described as an "unsupervised" process, because PCA "ignores" class labels and its goal is to find the directions (the so-called principal components) that maximize the variance in a dataset. In contrast to PCA, LDA is "supervised" and computes the directions ("linear discriminants") that will represent the axes that maximize the separation between multiple classes.

A dimension of the feature extracted from each signal segment may be relatively high. Thus, to save calculation time and increase a calculation accuracy, the authentication apparatus generates the first feature indication by performing dimension reduction processing with respect to the extracted feature.

In operation 102, the authentication apparatus generates a feature vector of the test ECG based on a pre-trained dictionary.

The authentication apparatus generates at least one second feature indication from the at least one first feature indication corresponding to the at least one signal segment of the test ECG based on the dictionary synchronously trained with a classifier. The authentication apparatus generates the at least one second feature indication corresponding to each of the at least one divided signal segment by performing group sparse coding, based on the dictionary, with respect to the first feature indication corresponding to the at least one signal segment obtained through the preprocessing. The authentication apparatus generates the feature vector of the test ECG based on the at least one second feature indication corresponding to the at least one signal segment.

In a group sparse coding performed to generate the feature indication, data is expressed as a linear combination of basic functions of a single group. Because coefficients used in the linear combination are sparse, a number of non-zero coefficients is significantly less than a total number of the coefficients. Group sparse coding is used to generate a feature indication of basic function data x of a small portion with representativeness detected in the basic functions of the single group. In an example, the basic functions of the group are referred to as a dictionary, each column of the dictionary is referred to as a codebook, and a coding coefficient is referred to as a new feature indication of the data x.

For example, x denotes a single item of d-dimensional data, and a dictionary D is a d x. J matrix. Here, $D=\{d_1, \ldots, d_j, \ldots, d_J\} \in \mathbb{R}^{d \times J}$, and each column $d_j$ of the dictionary D denotes a single basic function. z denotes a coefficient of the data x obtained based on the dictionary D, and $x = \sum_{j=i}^{J} z_j d_j$, $z \in \mathbb{R}^J$. The coding coefficient z is referred to as the new feature indication of the data x. The authentication apparatus generates a new feature indication from the at least one first feature indication corresponding to the at least one signal segment of the ECG based on group sparse coding using the dictionary. The new feature indication corresponds to the second feature indication.

Training of the dictionary based on group sparse coding is applicable to various fields. Classifying is a determination of a category to which unknown data belongs. Assuming that a dictionary with respect to each category is pre-constructed, a category is associated with a new single item of data. In this example, the data is expressed based on an optimally sparse dictionary with respect to the corresponding category. Training of a dictionary is enabling or teaching a dictionary to learn basic functions of a single group to code or satisfactorily indicate a signal provided as a training sample.

The authentication apparatus generates a new feature indication of the preprocessed ECG based on the dictionary. As a level of discrimination of the trained dictionary with respect to the feature increases, an accuracy of an authentication result increases.

In operation 103, the authentication apparatus generates a classification result indicative of the test ECG based on the generated feature vector and the pre-trained classifier.

Figure 3:
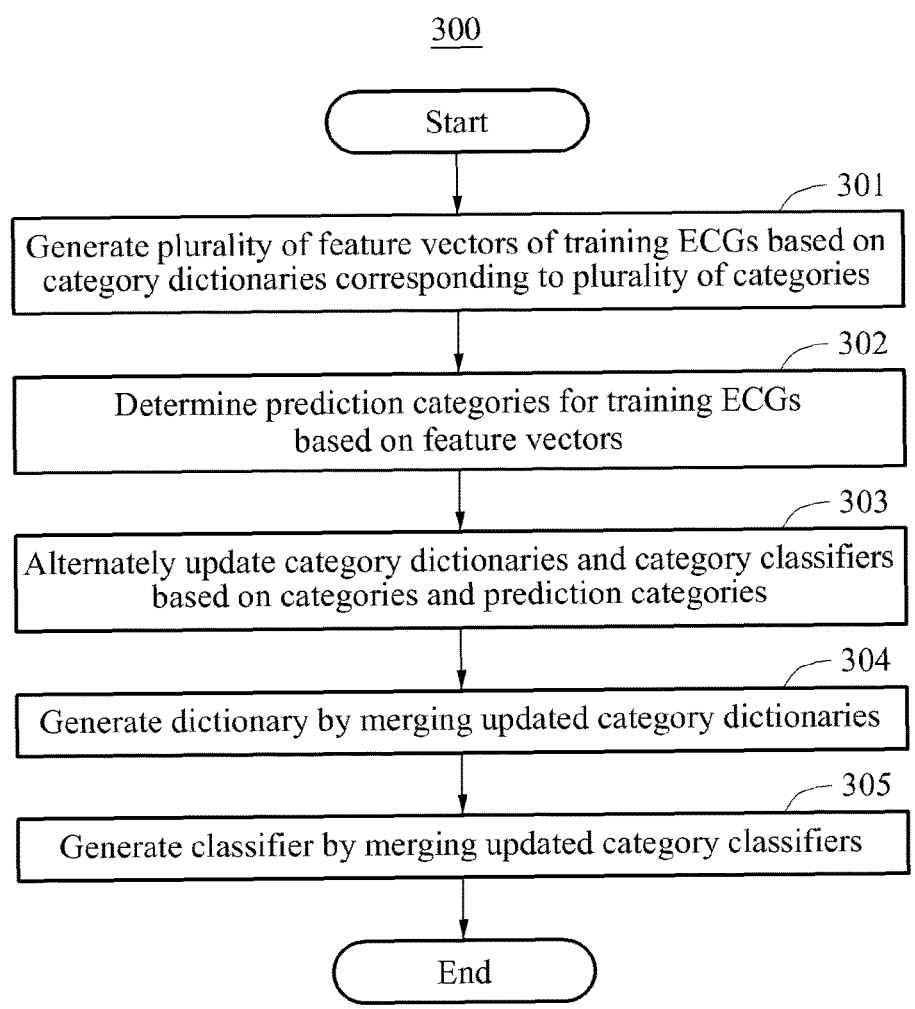
FIG. 3 is a flowchart illustrating a training method for ECG-based authentication, in accordance with an embodiment.
Figure 4:
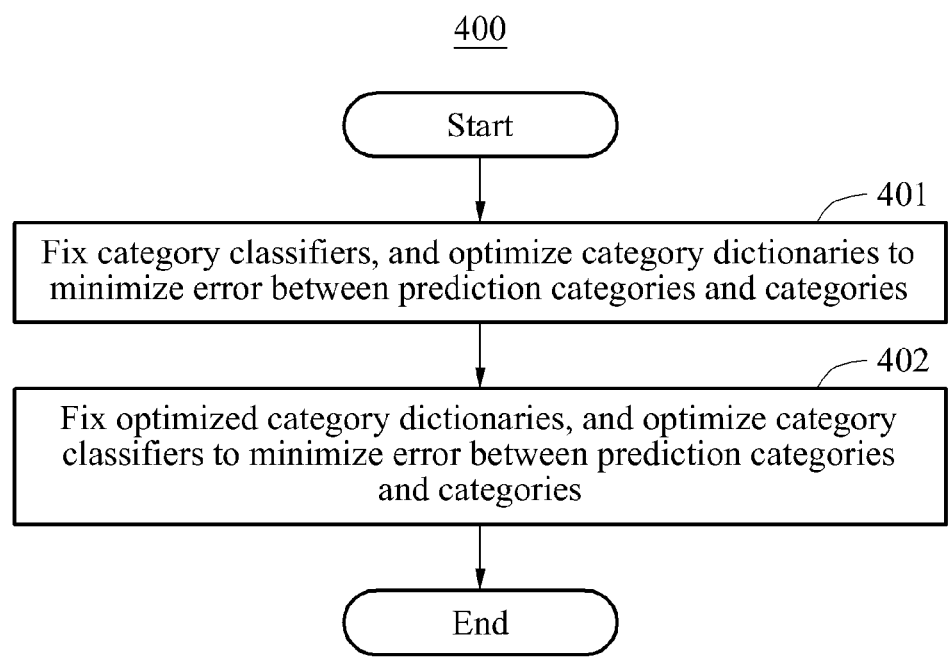
FIG. 4 is a flowchart illustrating alternately updating category dictionaries and category classifiers, in accordance with an embodiment.
Figure 5:
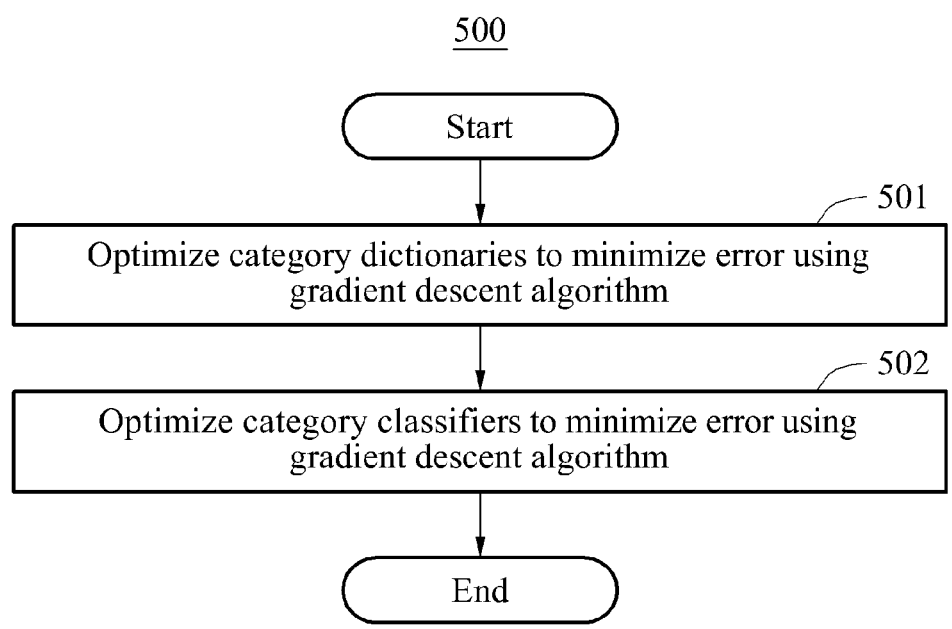
FIG. 5 is a flowchart illustrating optimizing category dictionaries and category classifiers, in accordance with an embodiment.

The classifier identifies a category to which the ECG belongs to based on the feature vector generated, which is based on the new feature indication (second feature indication) extracted through the dictionary. Referring to FIGS. 3 through 5, an example to synchronously train a dictionary and a classifier will be described. The authentication apparatus trains the dictionary and the classifier, or a separate apparatus trains the dictionary and the classifier, which are then loaded by the authenticated apparatus. However, the training apparatus is not limited thereto.

In operation 104, the authentication apparatus performs authentication with respect to the test ECG based on the generated classification result.

The authentication apparatus determines whether the test ECG passes authentication based on the classification result of the test ECG using a plurality of schemes. For example, a scheme calculates a mean value of feature indications of divided signal segments, and generates a classification result by inputting the calculated mean value into the classifier is used. The scheme is vulnerable to a noise effect and; thus, decreasing the accuracy thereof. The authentication apparatus determines whether the test ECG passes authentication through a decision based on a voting mechanism. In an example based on the voting mechanism, the authentication apparatus determines whether the test ECG passes authentication based on a vote of each category of all divided signal segments of the test ECG to reduce the noise effect. In an example, the authentication apparatus calculates a similarity between the classification result of the test ECG and a classification result of a reference ECG, and determines whether the test ECG passes authentication based on a result of the calculating. An example based on a decision based on a voting mechanism will be described with reference to FIG. 7.

A process of preprocessing the reference ECG and obtaining a classification result with respect to the preprocessed reference ECG based on the dictionary and the classifier is simultaneously performed with a process that processes the test ECG. In another example, the process of processing the reference ECG is first performed, and a classification result generated by the processing is pre-stored. The authentication apparatus obtains the pre-stored classification result and uses the obtained classification result in the process to perform authentication with respect to the test ECG. However, a point in time at which the reference ECG is processed is not limited thereto. In other words, a predetermined time period may lapsed prior to the performing of the authentication with respect to the test ECG. In the alternative, immediately after the obtaining of the classification result, the process to perform the authentication is executed.

The ECG-based authentication method uses the dictionary and the classifier which are synchronously trained. Synchronous training enables the dictionary to extract a feature with high-level discrimination and the classifier to generate a high-accuracy classification result by mutually using the dictionary and the classifier.

FIG. 3 is a flowchart 300 illustrating a training method for ECG-based authentication, in accordance with an embodiment.

Referring to FIG. 3, in operation 301, a training apparatus generates a plurality of feature vectors to train ECGs based on category dictionaries corresponding to a plurality of categories. The training apparatus divides each of the training ECGs into at least one signal segment by preprocessing the training ECGs belonging to different categories.

The training ECGs are obtained from ECGs of a plurality of entities, for example, people. In an example to classify an ECG, each entity corresponds to a single category. Classification of the ECG is used to authenticate or verify an identity. In another example, a plurality of entities having the same features corresponds to a single category. In an example, classification of the ECG is applicable to identify heart disease. However, the example of classifying the ECG based on a category is not limited thereto, and may be applied in various ways. Hereinafter, in classification in which a single entity corresponds to a single category, an example of using classification of an ECG to authenticate or verify the identity will be described.

The training apparatus obtains the plurality of training ECGs. As described with reference to FIG. 1, the training apparatus divides each of the training ECGs into at least one signal segment by preprocessing the obtained training ECGs. The example described above is applicable to the preprocessing process, and thus duplicated descriptions are omitted for conciseness. The training apparatus divides each training ECG into the at least one signal segment, and generates a feature indication with respect to the at least one divided signal segment.

For example, the training apparatus obtains ECGs of C entities as training ECGs. When the training apparatus preprocesses or divides the training ECGs into a plurality of signal segments, extracts features, and performs dimension reduction processing on the extracted features, each C entity is expressed as $X_c = \{X_1, \ldots X_i, \ldots, X_{N_c}\}$. In an example, $x_i \in R^d$, d denotes a feature dimension of a feature indication of each divided signal segment, and $N_c$ denotes a number of feature indications belonging to signal segments of a c-th entity. When sequentially arranging signal segments of all of the C entities, all training ECGs are expressed by feature indications of $X = \{X_1, \ldots, X_c, \ldots, X_C\}$. In an example, $X \in R^{d \times N}$, and N denotes a total number of all divided signal segments.

The training apparatus synchronously performs iterative training with respect to a category dictionary and a category classifier, corresponding to each category, based on the preprocessed training ECGs. The training apparatus sets the category dictionary and the category classifier corresponding to each category, and obtains the dictionary and the classifier based on the category. The training apparatus obtains the category dictionary and the category classifier corresponding to each category, the category dictionary, and the category classifier to identify a feature at a high level, using label information of a divided signal segment. The label information is a most significant medium to determine a feature as a classification result with respect to a signal segment.

In a case in which a method to synchronously train the category dictionary and the category classifier is not utilized, a relatively few codebooks are used to reconstruct an apparatus to identify features. As a result, discrimination with respect to features decreases. Further, in a case that the dictionary is trained with all of the training data, many data items of training data belonging to other categories are unnecessary to determine samples of a predetermined category. In addition, in a case in which a label to train data is not utilized for training, discrimination with respect to features decreases.

A feature indication with higher discrimination is obtained using a dictionary associated with a category. Further, robust identification with respect to an entity or a person is provided by utilizing label information being a medium that provides high-level feature discrimination.

When the training apparatus preprocesses the training ECGs, in other words, when the training apparatus divides the training ECGs into a plurality of signal segments, extracts features, and performs dimension reduction processing, each entity is expressed as follows: $X_c = \{X_1, \ldots, X_i, \ldots, X_{N_c}\}$.

In response to D denoting a dictionary, the dictionary is expressed as follows: $D = \{D_1, \ldots, D_c, \ldots, D_C\} \in R^{d \times J}$.

In an example, $D_c \in R^{d \times J_c}$ denotes a category dictionary corresponding to a c-th category, for example, a c-th entity. The category dictionary is also simply referred to as a c-th category dictionary. $D_c$ is expressed by $D_c = \{d_{1_c}, \ldots, d_{j_c}, \ldots, d_{J_c}\} \in R^{d \times J}$.

When the c-th entity is expressed as $X_c$, based on a feature indication of a divided signal segment, a new feature indication is extracted from $X_c$ through $D_c$-based group sparse coding. $X_c$ is expressed by $X_c = \sum_{j_c=1}^{J_c} z_{j_c} d_{j_c}$, $z \in R^J$.

In an example, $d_{j_c}$ denotes a single codebook of the c-th category, and $z_{j_c}$ denotes a coding coefficient which is the new feature indication, for example, a second feature indication, of $X_c$. $J_c$ denotes a number of codebooks of the c-th category dictionary, and J denotes a total number of codebooks of the dictionary D.

The training apparatus generates a new feature indication of X using group sparse coding. When the dictionary D is provided, z is deduced by performing group sparse coding with respect to X and is expressed by Equation 1.

$$z = \arg\min_z \frac{1}{2} \left\| x - \sum_{c=1}^{C} D_c z_c \right\|_2^2 + \mu \sum_{c=1}^{C} \| z_c \|_2 \qquad \text{[Equation 1]}$$

$$= \arg\min_z \frac{1}{2} \| x - D_z \|_2^2 + \mu \sum_{c=1}^{C} \| z_c \|_2$$

In Equation 1, $z \in R^J$, $z_c \in R^{J_c}$, and $z_c$ denote a coding coefficient corresponding to the c-th category dictionary among z. $\mu$ denotes a weight parameter. A range of $\| z_c \|_2$ restricts a category corresponding to a codebook used for reconstruction and, as a result, needs to be narrow. For example, a non-zero element of z deduced through group sparse coding with respect to $X_c$ based on a feature indication of a signal segment belonging to the c-th category belongs to a dimension corresponding to the c-th category dictionary. In this example, a calculation error caused by training data unrelated to identification is reduced. When the dictionary D is provided, z corresponding to each divided signal segment is obtained through Equation 1. The training apparatus generates second feature indications by performing group sparse coding, based on category dictionaries, with respect to the training ECGs, and generates feature vectors based on the second feature indications corresponding to divided signal segments.

In operation 302, the training apparatus determines prediction categories for the training ECGs based on the plurality of feature vectors of the training ECGs. To sufficiently use label information of a signal segment, a target function used to iterate synchronous training with respect to a dictionary and a classifier reflect label information and a category of a training ECG. The target function is designed using various application schemes, and is not limited to examples set forth herein.

The target function to minimize an error function between a prediction category and an actual category of a training ECG is set. The error function is expressed by Equation 2.

$$L = \min_{D,W} \alpha \|Z(D)^T W - G\| + \|W\|_F^2 \quad \text{[Equation 2]}$$
$$\text{s.t.} Z = [z_1, \cdots, z_N]$$

In Equation 2, α denotes a weight parameter, $W \in R^{J \times C}$ denotes a regression classifier, and $W_C$, being a predetermined single column of W, denotes a classifier of a corresponding category. G denotes an actual category corresponding to all divided signal segments, and is expressed as a label matrix. Among G, $G_C^i=1$ indicates that an i-th signal segment corresponds to a c-th category, for example, a category belonging to a c-th entity. Conversely, $G_C^i=0$ indicates that the i-th signal segment does not correspond to the c-th category. A first term $\|Z(D)^T W - G\|$ of Equation 2 denotes prediction errors of all signal segments, and $Z(D)^T W$ denotes a single N×C-dimensional matrix, which is a probability distribution of all signal segments with respect to all labels. Minimizing $\|Z(D)^T W - G\|$ minimizes an error between a prediction category and an actual category. A second term $\|W\|_F^2$ of Equation 2 is used to prevent overfitting.

In operation 303, the training apparatus alternately updates the category dictionaries and category classifiers based on the actual categories and the prediction categories. Referring to Equation 2, Z is a negative function of the dictionary D, and $Z_n$ is obtained from Equation 1. Thus, variable factors in Equation 2 are D and W. When the dictionary Z is provided, the training apparatus obtains feature vectors of the training ECGs through Equation 1, based on group sparse coding. The training apparatus obtains the classifier W through Equation 2, fixes the classifier W, optimizes the dictionary D through Equation 2, fixes the optimized dictionary D, and optimizes the classifier W through Equation 2. By iteratively performing optimization, as described above, the training apparatus enables the dictionary D and the classifier W to simultaneously reach local optimization. Also, the training apparatus obtains a category dictionary $D_c$ and a category classifier $W_c$ for each entity or that correspond to each entity. By iteratively performing synchronous training of the dictionary and the classifier to extract features and classify categories, the training apparatus promotes training of the dictionary and the classifier mutually.

In operation 304, the training apparatus generates a dictionary by merging the updated category dictionaries. The training apparatus obtains category dictionaries $D_c$, where, c=1, . . . , C, with respect to C categories updated through iterative training, generates a dictionary D in which the category dictionaries are merged in an arrangement, and expresses the dictionary D as $D=\{D_1, \ldots, D_c, \ldots, D_C\} \in R^{d \times J}$.

In operation 305, the training apparatus generates a classifier by merging the updated category classifiers. The training apparatus obtains the classifier using a method similar to that used to merge the category dictionaries.

FIG. 4 is a flowchart 400 illustrating alternately updating category dictionaries and category classifiers.

Referring to FIG. 4, in operation 401, a training apparatus fixes category classifiers, and optimizes category dictionaries to minimize an error between prediction categories and actual categories.

The training apparatus initializes a category dictionary corresponding to each category. To obtain category dictionaries and category classifiers corresponding to a plurality of categories through Equations 1 and 2, a classifier is obtained by fixing a dictionary. Thus, each category dictionary is initialized.

Various schemes are used to initialize the category dictionaries. The training apparatus generates a plurality of clusters by clustering preprocessed training ECGs based on a category. In an example, a k-means clustering scheme is utilized. Because various types of clustering schemes are used, examples are not limited to a scheme of applying clustering. The training apparatus generates the initialized category dictionaries by normalizing centers of the clusters generated by clustering.

In operation 402, the training apparatus fixes the optimized category dictionaries, and optimizes the category classifiers to minimize the error between the prediction categories and the actual categories.

The training apparatus synchronously updates the category dictionaries and the category classifiers using a method to minimize an error function between the prediction categories and the actual categories of the training ECGs based on the initialized category dictionaries. In accordance with an example, the training apparatus generates an initialized dictionary by arranging the initialized category dictionaries corresponding to all categories. The training apparatus generates a feature vector of each training ECG through group sparse coding of Equation 1, based on the initialized dictionary. The training apparatus obtains a classifier W based on the generated feature vector and Equation 2. The training apparatus optimizes a dictionary D based on the obtained classifier W and Equation 2. The training apparatus optimizes the classifier W based on the optimized dictionary D and Equation 2. By iterating the above calculation process, the dictionary D and the classifier W are optimized. In one example, Equation 2 is used to minimize the error function between the prediction categories and the actual categories of the training ECGs.

The training apparatus terminates the updating in response to the optimizing of the category dictionaries and the optimizing of the category classifiers and in response to satisfying a predefined condition. The training apparatus outputs the updated category dictionaries and the updated category classifiers. The performances of the obtained dictionary and the obtained classifier are expected to increase as an iteration count of the updating increases. However, the increase in the iteration count influences a calculation rate. Further, accuracies of the updated dictionary and the updated classifier may exceed a required level. Thus, in response to a proper condition being satisfied, the iteration of the updating is terminated, and the updated dictionary and the updated classifier are output.

The predefined condition includes at least one of a condition in which an iteration count reaches a predefined value, a condition in which a value of an error function between a prediction category and an actual category of an ECG is less than a predefined first value, and a condition in which a variation in the value of the error function is less than a predefined second value. In response to the predefined condition being satisfied, the training apparatus terminates the iteration of the synchronous training, and outputs a category dictionary and a classifier corresponding to each category.

FIG. 5 is a flowchart 500 illustrating optimizing category dictionaries and category classifiers, in accordance with an embodiment.

To derive an optimized dictionary and an optimized classifier, various types of calculation schemes are used. A training apparatus synchronously and iteratively calculates a dictionary and a classifier using a gradient descent algorithm. In accordance with alternative embodiments, other optimization algorithms may be used to optimize the dictionary and the classifier. Although an example to use the gradient descent algorithm is described with reference to FIG. 5, the calculation scheme for optimization is not limited thereto.

In operation 501, the training apparatus optimizes category dictionaries to minimize an error between prediction categories and actual categories of training ECGs using the gradient descent algorithm.

As described above, the training apparatus generates a feature vector of each training ECG through group sparse coding using each signal segment of the corresponding training ECG and based on a current dictionary. In a case of initially performing optimization, the current dictionary corresponds to an initialized dictionary. Updating for a subsequent iteration, the current dictionary corresponds to a dictionary optimized through previous synchronous training.

The training apparatus performs group sparse coding with respect to each training ECG by applying the current dictionary to Equation 1, and generates the feature vector corresponding to each training ECG. In an illustrative example, a second feature indication, with respect to each signal segment, is generated based on the current dictionary. A coding efficient, through group sparse coding, is the second feature indication of each signal segment. As described above, data corresponding to a category poorly or not associated with a training ECG causes a calculation error. However, using group sparse coding decreases the calculation error through a reconstructed codebook.

In operation 502, the training apparatus optimizes category classifiers to minimize the error using the gradient descent algorithm. The training apparatus updates each category classifier using the gradient descent algorithm based on the feature vector and an error function.

An initial value of a classifier W is calculated through Equation 2. The training apparatus obtains a derivative with respect to the classifier W from Equation 2 using a feature vector Z generated based on the initialized dictionary. In response to the derivative being set to "0", the classifier W is obtained as expressed by $W=\alpha(\alpha ZZ^T+\beta 1)^{-1}ZY$. In an example, I denotes a unit matrix of a dimension equal to a total dimension of a dictionary D, and $\alpha$ and $\beta$ are parameters of all constants. Y denotes an actual label of each divided signal segment, and is an already known value. In a state in which Z and Y are known, the classifier W is calculated. The derived classifier W is initialized in an iterative synchronous training process.

The training apparatus fixes the current dictionary D based on Equation 2, and obtains $$\frac{\partial L}{\partial W}$$

by calculating the derivative with respect to the classifier W. The classifier W is updated based on a formula of a gradient descent algorithm $$W = W - \alpha \cdot \frac{\partial L}{\partial W}.$$

In one example, $\alpha$ denotes a step size in search in a gradient direction. The training apparatus updates each category dictionary using the gradient descent algorithm based on the updated category classifier and the error function.

The training apparatus fixes the updated classifier W, and obtains a derivative with respect to the dictionary D. Equation 2 does not include an explicit expression related to D, but includes an explicit expression related to Z. Z is a function of the dictionary D, and Z includes a plurality of zs. Thus, each z corresponds to the function of the dictionary D. Accordingly, the derivative $$\frac{\partial L_n}{\partial D}$$

of the dictionary D with respect to an error function of an n-th training ECG is calculated using a fixed point implicit difference method. When performing the calculation, the training apparatus randomly arranges each signal segment, and calculates a gradient in a predetermined order after the arrangement is performed.

When obtaining $$\frac{\partial L_n}{\partial D},$$

the training apparatus obtains derivatives $$\frac{\partial L_n}{\partial z_n} \text{ and } \frac{\partial z_n}{\partial D}$$

using a chain rule, and obtains $$\frac{\partial L_n}{\partial D}$$

by multiplying the derivatives. In response to $$\frac{\partial L_n}{\partial D}$$

being obtained, the training apparatus updates the dictionary D based on a formula of a gradient descent algorithm, $$D = D - \alpha \cdot \frac{\partial L_n}{\partial D}.$$

In an example, α denotes a step size in search in a gradient direction.

In a process of applying the gradient descent algorithm to the dictionary, in an example in which only a derivative $$\frac{\partial L_n}{\partial D}$$

of the dictionary D is obtained with respect to a value of an error function of an n-th training sample, and a derivative $$\frac{\partial L_n}{\partial D}$$

of the dictionary D is not obtained with respect to values of error functions of all training samples, the training apparatus reduces error by iterating the synchronous training by randomly arranging signal segments with respect to a plurality of training ECGs, and calculating a gradient in a predetermined order after each arrangement is performed.

An example of synchronously training the dictionary and the classifier is described above. As described above, because a category dictionary is trained with respect to each category, a calculation error caused by data unassociated with training decreases. In an example, by performing group sparse coding, a codebook used for reconstruction corresponds to as few categories as possible when determining a coding coefficient z. Through the foregoing and in accordance with an embodiment, data is expressed using an associated category dictionary.

The training apparatus obtains a feature having high-level discrimination by utilizing label information to train the dictionary, setting minimization of an error function between a prediction category and an actual category of a training ECG to be a target function, and synchronously training of the dictionary and the classifier.

Figure 6:
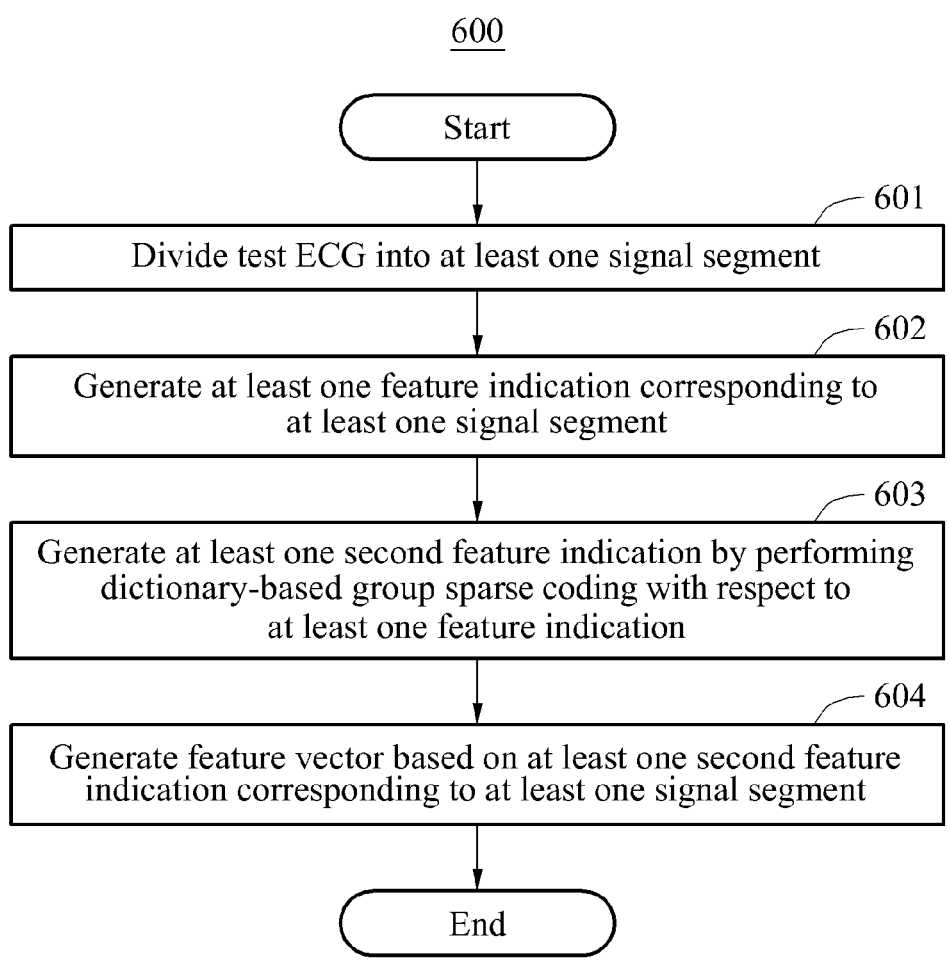
FIG. 6 is a flowchart illustrating generating a feature vector corresponding to a test ECG, in accordance with an embodiment.

FIG. 6 is a flowchart 600 illustrating generating a first feature vector corresponding to a test ECG, in accordance with an embodiment.

A dictionary and a classifier trained using the scheme as described above are used to extract a feature from a test ECG and classify an entity or a person during a test or authentication operation. In operation 601, an authentication apparatus divides a test ECG into at least one signal segment.

In operation 602, the authentication apparatus generates at least one first feature indication corresponding to the at least one signal segment. In an example, preprocessing with respect to the ECG as described above is applied to generate the first feature indication.

In operation 603, the authentication apparatus generates at least one second feature indication by performing group sparse coding, based on a dictionary and with respect to the at least one first feature indication. In an embodiment, the example described above is applied to the dictionary and group sparse coding. The second feature indication is generated through Equation 1.

In operation 604, the authentication apparatus generates a feature vector based on the at least one second feature indication that corresponds to the at least one signal segment. For example, in response to a feature indication of a signal segment corresponding to a preprocessed test ECG is expressed as $S=\{_1, \ldots, S_p, \ldots, S_P\}$, and the authentication apparatus generates a feature vector $Z_s=\{z_1^s, \ldots, z_p^s, \ldots, z_P^s\}$ through group sparse coding with respect to S based on Equation 1. In an example, P denotes a number of signal segments corresponding to a test ECG.

The authentication apparatus classifies the test ECG based on the feature vector and a classifier W. The authentication apparatus calculates a label of each divided signal segment based on the classifier W and $I_P^S = \arg\max_i (z_p^S)^T W(:,i)$. In an example, the label is a classification result with respect to each signal segment of the test ECG, and $I_p^S$ denotes a label corresponding to the test ECG.

Figure 7:
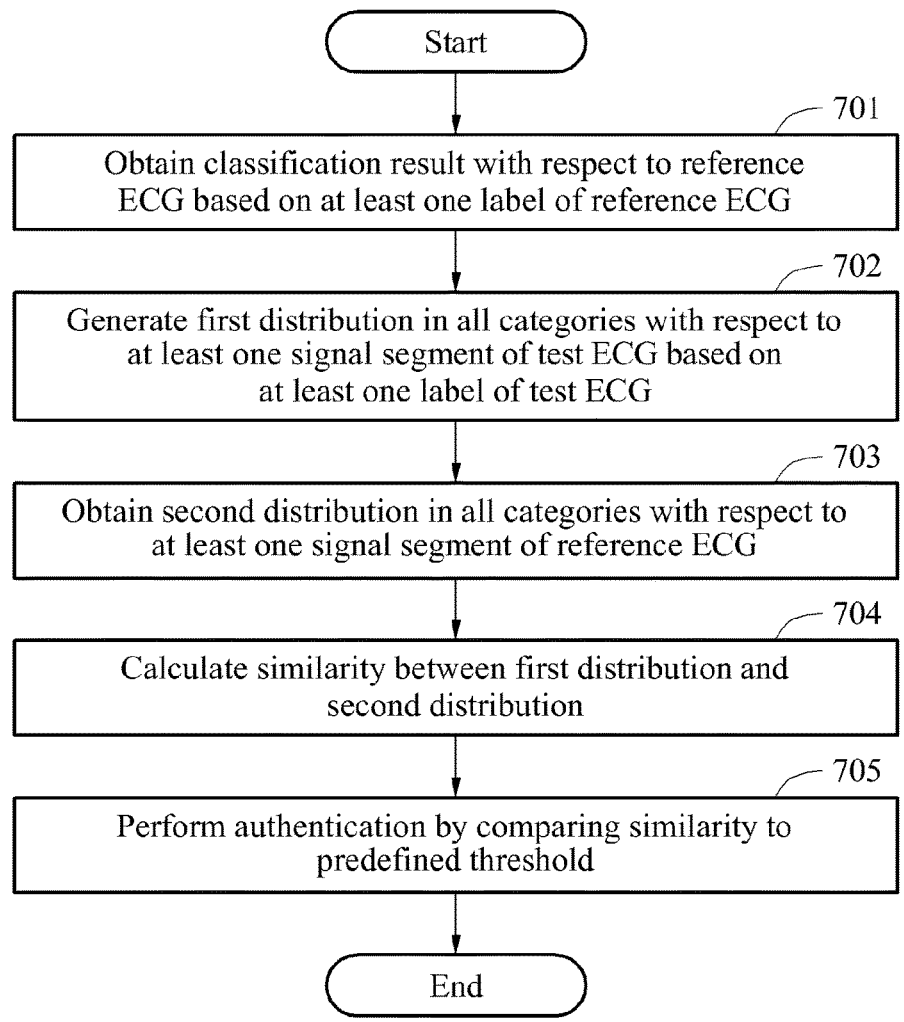
FIG. 7 is a flowchart illustrating authentication with respect to an ECG, in accordance with an embodiment.

FIG. 7 is a flowchart 700 illustrating authentication with respect to an ECG, in accordance with an embodiment.

An authentication apparatus determines whether a test ECG passes authentication based on a classification result of the test ECG. In operation 701, the authentication apparatus obtains a classification result with respect to a reference ECG based on at least one label of the reference ECG.

A classification result of each signal segment obtained based on a dictionary and a classifier with respect to the reference ECG is obtained from a classification result corresponding to pre-stored data. In an alternative, the classification of each signal segment is simultaneously obtained processing of the test ECG in an authentication operation. In response to a feature indication of a signal segment of a preprocessed reference ECG being $Y=\{Y_1, \ldots, Y_q, \ldots, Y_Q\}$, the authentication apparatus generates a new feature vector $Z_Y=\{z_1^Y, \ldots z_q^Y, \ldots z_Q^Y\}$ through group sparse coding with respect to Y through Equation 1. In an example, Q denotes a number of signal segments of the reference ECG.

The authentication apparatus calculates a label of each signal segment with respect to a classifier W and $I_Q^Y = \arg\max_i (z_q^Y)^T W(:,i)$. In an example, the label is a classification result with respect to each signal segment of the reference ECG, and $I_q^Y$ denotes a label corresponding to the reference ECG.

The authentication apparatus determines whether the test ECG passes authentication by performing authentication based on a voting mechanism for a classification result of the test ECG and a classification result with respect to the reference ECG.

In operation 702, the authentication apparatus generates a first distribution in all categories of at least one signal segment of the test ECG based on at least one label of the test ECG. The first distribution includes a number of signal segments belonging to each of a plurality of categories.

In detail, the authentication apparatus calculates a number of votes, for example, a distribution, with respect to each category of each test ECG based on the label corresponding to the test ECG. For example, the test ECG includes P signal segments in total, and k signal segments are predicted to correspond to a c-th category, for example, a c-th entity. In this example, a number of votes corresponding to the c-th category is calculated by $$h_c^s = \frac{k}{p}.$$

The authentication apparatus obtains a first distribution $H^S = [h_1^S, \ldots h_c^S, \ldots h_C^S]$ or a histogram corresponding to the test ECG based on the number of votes with respect to each category.

In operation 703, the authentication apparatus obtains a second distribution in all categories of at least one signal segment of the reference ECG. The second distribution includes a number of reference signal segments belonging to each of the plurality of categories. Similar to the above-described scheme, a second distribution $H^Y = [h_1^Y, \ldots h_c^Y, \ldots h_C^Y]$ corresponding to the reference ECG is obtained based on a number of votes $h_c^Y$, for example, a distribution, with respect to each category of the reference ECG.

In operation 704, the authentication apparatus calculates a similarity between the first distribution and the second distribution. Various schemes are applicable to the similarity calculation. The authentication apparatus calculates a similarity between two distributions or histograms using a scheme of intersecting the histograms. For example, the similarity is calculated by $$\text{Similarity}(H^S, H^Y) = \sum_{c=1}^{C} \min(\overline{H_c^S}, \overline{H_c^Y}).$$

In an example, $$\overline{H_c^S} = \frac{1}{P} h_c^S, \text{ and } \overline{H_c^Y} = \frac{1}{Q} h_c^S.$$

In operation 705, the authentication apparatus performs authentication by comparing the similarity to a predefined threshold. The authentication apparatus compares the similarity to the predefined threshold to verify whether the similarity is greater than or equal to the predefined threshold, and determines whether the test ECG passes authentication based on a comparison result.

In response to the similarity being greater than or equal to the predefined threshold, the authentication apparatus determines that the test ECG and the reference ECG are sufficiently similar to each other, and that the test ECG passes authentication. Conversely, in response to the similarity being less than the predefined threshold, the authentication apparatus determines that a difference between the test ECG and the reference ECG is relatively great, and rejects authentication with respect to the test ECG is rejected.

Although operations are described in an order specified in the accompanying drawings, examples are not limited thereto. In detail, the operations performed at the authentication apparatus do not need to be performed in the order, or not all of the operations need to be performed. For example, in FIG. 3, operation of merging the category classifiers may be performed in advance or prior to merging the category dictionaries. In another embodiment, operation of merging the category classifiers may be performed concurrently operation with merging of the category dictionaries. In FIG. 7, operation of obtaining the second distribution corresponding to the reference ECG may be performed in advance or prior to generating the first distribution corresponding to the test ECG. Further, additionally or selectively, a portion of operations is omitted, a single operation is performed by merging a plurality of operations, and/or a plurality of operations are performed by dividing a single operation into a plurality of operations.

As described above, an ECG-based authentication method is applicable to verify identity. There may multiple examples of a scheme to verify an identity. A reference ECG corresponding to a user having a preset authority is pre-obtained. For example, the user has an access authority or a use authority with respect to a predetermined resource. The obtained reference ECG is stored and used as a basis to determine whether the user has a preset authority.

When a user to be authenticated tries to have access, a test ECG of the user is obtained, and authentication with respect to the test ECG is performed using an authentication method. In response to the test ECG passing authentication, the user is determined to have a preset authority. For example, a smart phone is used to obtain and store a reference ECG corresponding to an owner of the smart phone. In a case in which the user tries to use the smart phone, authentication with respect to a test ECG is performed using the authentication method. In response to the user being authenticated or identified as the owner of the smart phone, the test ECG passes authentication, and the user is allowed to use the smart phone or resources in the smart phone.

A plurality of users may have preset authorities. In this example, reference ECGs corresponding to the plurality of users need to be stored. When a user needs to be authenticated, a test ECG from the user is obtained and authentication with respect to the test ECG is performed based on the pre-stored reference ECGs using the authentication method. Once the test ECG passes authentication, the user is determined to have a preset authority. For example, a gate security device of a predetermined complex obtains and stores reference ECGs corresponding to all residents of the complex. In response to a visitor trying to access the complex, the gate security device obtains a test ECG from the visitor and performs authentication with respect to the test ECG by exploring the pre-stored reference ECGs using the authentication method. In response to the visitor being one of the residents, the test ECG passes authentication, and the gate security device is unlocked.

In another example, reference ECGs corresponding to specific users, for example, all employees of a predetermined company or all students of a predetermined school, are pre-obtained. Related information of the users corresponding to the reference ECGs are merged with the reference ECGs, stored, used as a basis to determine an identity of a user, and used to search for or record the related information of the users. When a user visits, a test ECG of the user is obtained, and authentication with respect to the test ECG is performed based on the pre-stored reference ECGs using the authentication method. In response to the test ECG passing authentication with respect to a predetermined reference ECG, an identity of the user is determined based on related information associated with the reference ECG, related information of the user is obtained, and the new information of the user is merged with the identity of the user and additionally recorded.

For example, an attendance monitoring device of a predetermined company obtains reference ECGs corresponding to all employees of the company, merges names of the employees with IDs of the employees, and stores the merged data. When an employee records an attendance, the attendance monitoring device obtains a test ECG of the employee, and performs authentication with respect to the test ECG based on the pre-stored reference ECGs using the authentication method. In response to the test ECG passing authentication compared to a reference ECG, a name and an ID of the employee associated with the reference ECG are retrieved and displayed on a screen. A time at which the employee arrives or leaves is merged with the ID of the employee, and the merged data is recorded and used as attendance information of the employee.

Figure 8:
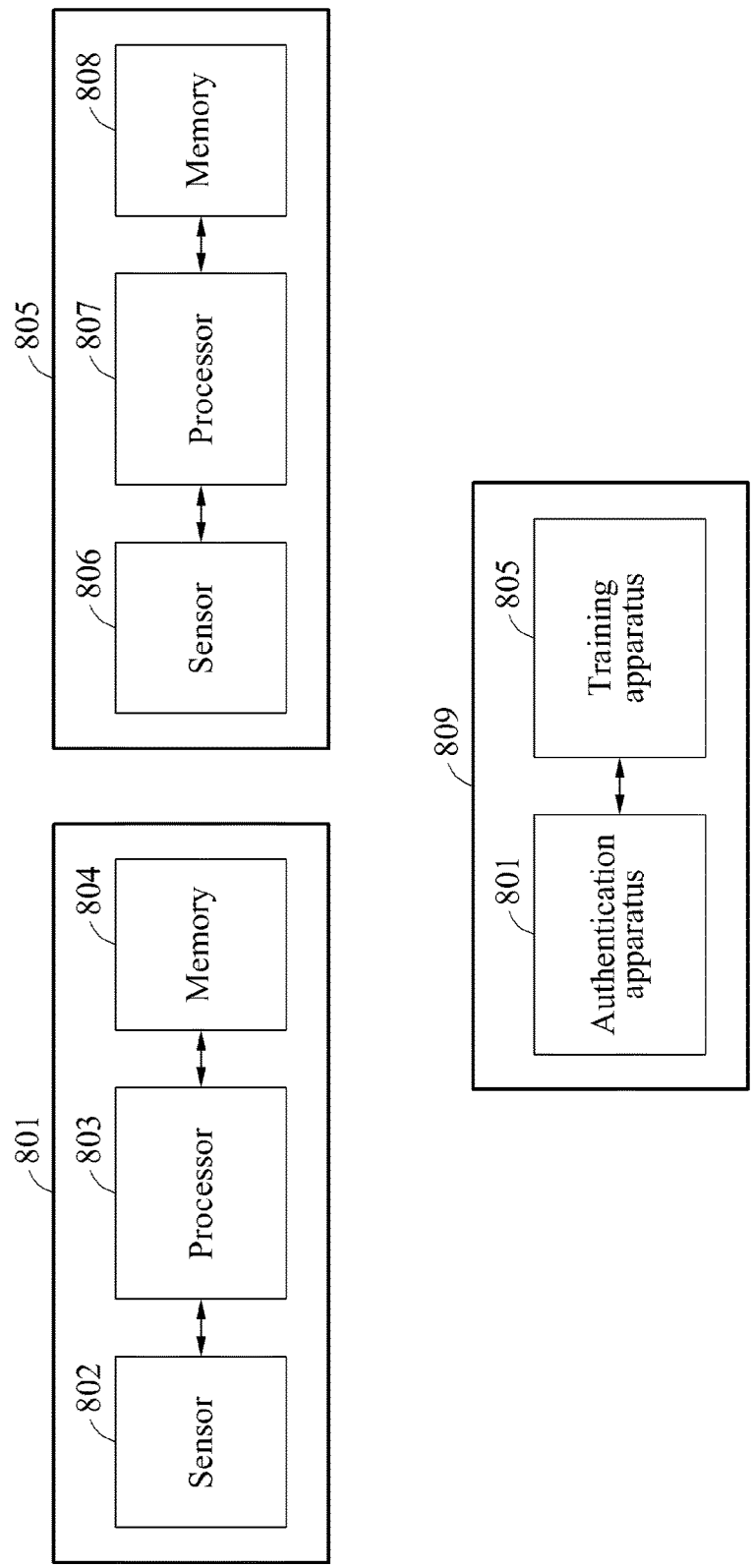
FIG. 8 is a block diagram illustrating an authentication apparatus and a training apparatus, in accordance with an embodiment.

FIG. 8 is a block diagram illustrating an authentication apparatus 801 and a training apparatus 805, in accordance with an embodiment.

Referring to FIG. 8, the authentication apparatus 801 includes a sensor 802, a processor 803, and a memory 804. The sensor 802 senses a test ECG from an entity, and the processor 803 obtains the test ECG of the entity through the sensor 802. The processor 803 generates a feature vector of the test ECG based on a pre-trained dictionary, generates a classification result with respect to the test ECG based on the feature vector and a pre-trained classifier, and performs authentication with respect to the test ECG based on the classifier result. The memory 804 is configured to record the pre-trained dictionary and the pre-trained classifier. The processor 803 is used to perform authentication with respect to the test ECG by loading information stored in the memory 804. Descriptions provided with reference to FIGS. 1 through 7 are applicable to the authentication apparatus 801, and thus duplicated descriptions will be omitted for conciseness.

Although the sensor 802, the processor 803, and the memory 804 are described as separate structural elements, a person skilled in the art will appreciate that the sensor 802, the processor 803, and the memory 804 may be combined into a single processor or controller and perform the functionality explained and illustrated with respect to each structural element. Furthermore, although the memory 804 is part of the authentication apparatus 801, a person skilled in the art will appreciate that the memory 804 may be an external structural element to the authentication apparatus 801.

The training apparatus 805 includes a sensor 806, a processor 807, and a memory 808. The sensor 806 senses training ECGs, and the processor 807 obtains the plurality of ECGs through the sensor 806. The processor 807 generates feature vectors of the training ECGs based on category dictionaries corresponding to a plurality of categories, determines prediction categories for the training ECGs based on the feature vectors, and alternately updates the category dictionaries and category classifiers based on the categories and the prediction categories. The memory 808 is configured to record the category dictionaries and the category classifiers, and the processor 807 trains a dictionary and a classifier by alternately updating the category dictionaries and the category classifiers recorded in the memory 808. Descriptions provided with reference to FIGS. 1 through 7 are applicable to the training apparatus 805, and thus duplicated descriptions will be omitted for conciseness.

Although the sensor 806, the processor 807, and the memory 808 are described as separate structural elements, a person skilled in the art will appreciate that the sensor 806, the processor 807, and the memory 808 may be combined into a single processor or controller and perform the functionality explained and illustrated with respect to each structural element. Furthermore, although the memory 808 is part of the training apparatus 805, a person skilled in the art will appreciate that the memory 804 may be an external structural element to the training apparatus 805.

The authentication apparatus 801 and the training apparatus 805 are separate as independent structural devices to operate separately. In an alternative embodiment, the authentication apparatus 801 and the training apparatus 805 are integrated as a single apparatus 809 and applicable to a smart device. The authentication apparatus 801 and the training apparatus 805 interoperate with each other, or operate separately as independent entities. Various applications may be made thereto.

The apparatuses, units, modules, devices, and other components illustrated in FIG. 8 that perform the operations described herein with respect to FIGS. 1 through 7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1 through 7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1 through 7 that perform the operations described herein with respect to FIG. 8 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method, comprising:
   generating a feature vector from an electrocardiogram (ECG) based on a pre-trained dictionary;
   generating a classification result of the ECG based on the feature vector and a pre-trained classifier;
   obtaining a classification result of a reference ECG comprising a reference signal segment; and
   performing authentication of the ECG based on a voting mechanism for the classification result of the ECG and the classification result of the reference ECG,
   wherein the performing of the authentication based on the voting mechanism comprises
      generating a first distribution comprising a number of signal segments belonging to each of a plurality of categories based on a label of the ECG,
      obtaining a second distribution comprising a number of reference signal segments belonging to each of the categories,
      calculating a similarity between the first distribution and the second distribution, and
      performing the authentication by comparing the similarity to a threshold.

2. The method of claim 1, wherein the dictionary and the classifier are trained synchronously.

3. The method of claim 1, wherein the dictionary comprises category dictionaries corresponding to categories, and
   the classifier comprises category classifiers corresponding to the categories.

4. The method of claim 3, wherein the dictionary and the classifier are synchronously trained by generating feature vectors to train ECGs based on the category dictionaries, determining prediction categories for the ECGs based on the feature vectors, and alternately updating the category dictionaries and the category classifiers based on the categories and the prediction categories.

5. The method of claim 1, wherein the generating of the feature vector comprises:
   determining coefficients of category dictionaries included in the dictionary for the ECG to be a linear combination of the category dictionaries; and
   generating the feature vector based on the coefficients.

6. The method of claim 1, wherein the generating of the feature vector comprises:
   dividing the ECG into a signal segment;
   generating a feature indication corresponding to the signal segment;
   generating a second feature indication by performing group sparse coding, based on the dictionary and the feature indication; and
   generating the feature vector based on the second feature indication.

7. The method of claim 6, wherein the feature indication is a linear combination of a portion of category dictionaries included in the dictionary, and
   the second feature indication comprises coefficients of the portion of the category dictionaries.

8. The method of claim 1, wherein the generating of the classification result comprises:
   generating a label corresponding to a classification result of a signal segment of the ECG based on the feature vector and the classifier; and
   generating the classification result of the ECG based on the label.

9. The method of claim 1, wherein the classification result of the reference ECG is obtained by applying the dictionary and the classifier to the reference ECG.

10. A training method, comprising:
    generating feature vectors of training electrocardiograms (ECGs) based on category dictionaries corresponding to categories;
    determining prediction categories for the training ECGs based on the feature vectors; and
    alternately updating the category dictionaries and category classifiers based on the categories and the prediction categories,
    wherein the updating comprises
       fixing the category classifiers and optimizing the category dictionaries to minimize an error between the prediction categories and the categories, and
       fixing the optimized category dictionaries and optimizing the category classifiers to minimize the error between the prediction categories and the categories,
    wherein the optimizing of the category dictionaries and the optimizing of the category classifiers are synchronously iterated.

11. The method of claim 10, wherein the generating comprises:
dividing each of the training ECGs into a signal segment;
generating a feature indication corresponding to the signal segment;
generating a second feature indication by performing group sparse coding, based on the category dictionaries, of the feature indication; and
generating the feature vectors based on the second feature indication corresponding to the signal segment.

12. The method of claim 10, wherein the optimizing of the category dictionaries comprises optimizing the category dictionaries to minimize the error using a gradient descent algorithm, and
the optimizing of the category classifiers comprises optimizing the category classifiers to minimize the error using the gradient descent algorithm.

13. The method of claim 10, further comprising:
terminating the updating in response to the optimizing of the category dictionaries and the optimizing of the category classifiers satisfying a condition; and
outputting the updated category dictionaries and the updated category classifiers,
wherein the condition comprises at least one of a condition in which an iteration count reaches a value, a condition in which the error is less than a first value, and a condition in which a variation in the error is less than a second value.

14. The method of claim 10, further comprising:
initializing the category dictionaries based on the training ECGs corresponding to the categories.

15. The method of claim 14, wherein the initializing comprises:
preprocessing the training ECGs;
generating clusters by clustering the preprocessed training ECGs based on the categories; and
generating the initialized category dictionaries by normalizing centers of the clusters.

16. The method of claim 15, wherein the preprocessing comprises:
dividing the training ECGs into a signal segment;
extracting a feature of the signal segment; and
generating a feature indication of the signal segment by performing dimension reduction processing of the feature.

17. The method of claim 16, wherein the dividing comprises:
filtering each of the training ECGs;
detecting a QRS wave of each of the filtered training ECGs; and
generating the at least one signal segment based on a result of the detecting.

18. The method of claim 10, further comprising:
initializing the category classifiers based on the feature vectors and the category dictionaries.

19. The method of claim 18, wherein the initializing comprises:
generating a probability distribution of the categories of the signal segment based on the feature vectors and the category dictionaries;
calculating a prediction error for the signal segment based on the probability distribution and an actual category of the signal segment;
obtaining category classifiers minimizing an error between the prediction categories and the categories based on the prediction error; and
generating the initialized category classifiers as the obtained category classifiers.

20. The method of claim 10, further comprising:
generating a dictionary by merging the updated category dictionaries; and
generating a classifier by merging the updated category classifiers.

21. A non-transitory computer-readable storage medium storing a program comprising instructions to cause a computer comprising a processor to perform:
generating a feature vector from an electrocardiogram (ECG) based on a pre-trained dictionary;
generating a classification result of the ECG based on the feature vector and a pre-trained classifier;
obtaining a classification result of a reference ECG comprising a reference signal segment; and
performing authentication of the ECG based on a voting mechanism for the classification result of the ECG and the classification result of the reference ECG,
wherein the performing of the authentication based on the voting mechanism comprises
generating a first distribution comprising a number of signal segments belonging to each of a plurality of categories based on a label of the ECG,
obtaining a second distribution comprising a number of reference signal segments belonging to each of the categories,
calculating a similarity between the first distribution and the second distribution, and
performing the authentication by comparing the similarity to a threshold.

22. An apparatus, comprising:
a sensor configured to receive an electrocardiogram (ECG); and
a processor configured to
generate a feature vector of the ECG based on a pre-trained dictionary;
generate a classification result of the ECG based on the feature vector and a pre-trained classifier
obtain a classification result of a reference ECG comprising a reference signal segment; and
perform authentication of the ECG based on a voting mechanism for the classification result of the ECG and the classification result of the reference EGG,
wherein the performing of the authentication based on the voting mechanism comprises
generating a first distribution comprising a number of signal segments belonging to each of a plurality of categories based on a label of the EGG,
obtaining a second distribution comprising a number of reference signal segments belonging to each of the categories,
calculating a similarity between the first distribution and the second distribution, and
performing the authentication by comparing the similarity to a threshold.

23. A training apparatus, comprising:
a sensor configured to receive training electrocardiograms (ECGs); and
a processor configured to
generate feature vectors of training ECGs based on category dictionaries corresponding to categories;
determine prediction categories for the training ECGs based on the feature vectors; and
alternately update the category dictionaries and category classifiers based on the categories and the prediction categories, wherein the updating of the category dictionaries and the category classifiers comprises fixing the category classifiers and optimizing the category dictionaries to minimize an error between the prediction categories and the categories, and fixing the optimized category dictionaries and optimizing the category classifiers to minimize the error between the prediction categories and the categories, wherein the optimizing of the category dictionaries and the optimizing of the category classifiers are synchronously iterated.

24. A method, comprising:

dividing an electrocardiogram (ECG) for user authentication into a signal segment;

generating a first feature indication corresponding to the signal segment;

generating a second feature indication by performing group sparse coding, based on a dictionary and the first feature indication;

generating a feature vector of the ECG based on the second feature indication corresponding to the signal segment;

generating a classification result indicative of the ECG based on the feature vector and a classifier;

obtaining a classification result of a reference ECG comprising a reference signal segment; and performing authentication of the ECG based on a voting mechanism for the classification result of the ECG and the classification result of the reference ECG, wherein the performing of the authentication based on the voting mechanism comprises generating a first distribution comprising a number of signal segments belonging to each of a plurality of categories based on a label of the EGG, obtaining a second distribution comprising a number of reference signal segments belonging to each of the categories, calculating a similarity between the first distribution and the second distribution, and performing the authentication by comparing the similarity to a threshold.

25. The method of claim 24, further comprising:

extracting a feature from the divided signal segment; and performing dimension reduction processing of the extracted feature.

26. The method of claim 24, wherein the generating of the classification result is based on a label corresponding to a classification result of the signal segment of the ECG based on the feature vector and the classifier.

27. The method of claim 24, further comprising:

synchronously training the dictionary and the classifier.

* * * * *